(12) United States Patent
Gorsuch et al.

(10) Patent No.: US 6,949,078 B2
(45) Date of Patent: * Sep. 27, 2005

(54) APPARATUS AND METHOD FOR SELECTIVE REDUCTION OF SEGMENTAL INTRACELLULAR AND EXTRACELLULAR EDEMA

(75) Inventors: Reynolds G. Gorsuch, Yountville, CA (US); Kris Venkat, Somerset, NJ (US)

(73) Assignee: Transvivo, Inc., Napa, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 10/357,068

(22) Filed: Jan. 31, 2003

(65) Prior Publication Data

US 2003/0114784 A1 Jun. 19, 2003

Related U.S. Application Data

(63) Continuation of application No. 09/799,466, filed on Mar. 5, 2001, now Pat. No. 6,632,192.

(51) Int. Cl.$^7$ .......................... A61M 37/00; A61M 5/00
(52) U.S. Cl. .................... 604/6.04; 604/6.09; 604/6.11; 604/9
(58) Field of Search ............................. 604/4.01, 5.01, 604/6.01, 6.04, 6.05, 6.06, 6.09, 7–10, 28, 506–7, 27, 29, 6.11, 6.12; 210/645–646

(56) References Cited

U.S. PATENT DOCUMENTS

| 4,411,792 A | 10/1983 | Babb .......................... 210/651 |
| 4,950,224 A | 8/1990 | Gorsuch et al. |
| 5,151,082 A | 9/1992 | Gorsuch et al. |
| 5,152,743 A | 10/1992 | Gorsuch et al. |
| 5,224,926 A | 7/1993 | Gorsuch et al. |
| 5,242,382 A | 9/1993 | Gorsuch et al. |
| 5,735,809 A | 4/1998 | Gorsuch |
| 5,744,031 A | * 4/1998 | Bene ..................... 210/321.71 |
| 5,968,004 A | 10/1999 | Gorsuch |
| 5,980,478 A | 11/1999 | Gorsuch et al. |
| 5,980,481 A | 11/1999 | Gorsuch |
| 6,200,485 B1 | * 3/2001 | Kitaevich et al. ........... 210/739 |

FOREIGN PATENT DOCUMENTS

EP        0 274 178 A1        7/1988

* cited by examiner

*Primary Examiner*—Angela D. Sykes
*Assistant Examiner*—Leslie Deak
(74) *Attorney, Agent, or Firm*—Knobbe, Martens, Olson & Bear, LLP

(57) ABSTRACT

Segmental edema is treated by inserting a plasma extraction filter device in a major vein of a body segment or servicing the body segment containing the edemic tissues, and inserting a return catheter in a major artery of the body segment affected or feeding the body segment from which plasma is extracted. Blood plasma and plasma proteins extracted from the edemic body segment through the plasma extraction filter fluids are directed to an ultrafiltration apparatus where plasma water is separated from the plasma proteins. Plasma proteins are returned to the body segment from which the plasma was extracted via the return catheter in the major artery of the subject body segment.

36 Claims, 3 Drawing Sheets

APPARATUS AND METHOD FOR SELECTIVE REDUCTION OF SEGMENTAL INTRACELLULAR AND EXTRACELLULAR EDEMA

RELATED APPLICATIONS

This application is a continuation of co-pending application Ser. No. 09/799,466 filed Mar. 5, 2001 now U.S. Pat. No. 6,632,192.

BACKGROUND OF THE INVENTION

Edema, by definition, is the presence of excess fluid in body tissue. An adult male weighing 70 kilograms is composed of about 50% fluid, nominally water, amounting to about 40 liters, approximately 25 liters of which is intracellular and about 15 liters extracellular. Edema occurs in both extracellular fluid compartments as well as intracellular fluid spaces. Although there are many causes of edema, the two most prevalent are heart failure and kidney disease nephrosis in which generalized systemic edema causes pulmonary failure with acute respiratory distress syndrome, and simultaneous pre-renal acute kidney failure. Fluid management systems for addressing such specific systemic conditions have been developed utilizing techniques and apparatus disclosed in U.S. Pat. Nos. 4,950,224, 5,151,082, 5,152,743, 5,224,926, 5,242,382, 5,735,809, 5,968,004, 5,980,478 and 5,980,481. The disclosures of the aforesaid patents are incorporated herein by reference.

A number of edemic conditions, although not systemic, occur in segmented sections of the body. For example, "Elephantitus" occurs when the lymph nodes in the lower extremities are blocked by infection, especially filarial nematodes resulting in localized edema. Blockage of lymph nodes by cancer, e.g., breast cancer, causes localized edema. Vascular bi-pass procedures can also induce severe localized edema. For treating such localized edema, it is far more preferable and proficient to treat the segment of the body affected rather than attempting to reduce systemic edema of the entire body which could result in negative side effects. However, current therapeutic methods for treating segmental edema involve complex physical therapy utilizing a modality of repeated massage techniques designed to enlist parallel lymphatic paths to relieve blocked lymph circulation. Such techniques are somewhat empirical in nature and have great variation in efficacy. These therapies also are used with special compression garments and/or bandages which must be continuously adjusted over time to fit changing needs of the patient. Oral and topical drugs such as Benzo-pyrones are often combined with the aforesaid therapeutic methods, resulting in long-term treatment, often six months to years before significant results are achieved.

SUMMARY OF THE INVENTION

The present invention is directed to means for the selective reduction of localized edemas in substantially reduced time for palliative results. The method of treating segmental edema according to the present invention comprises inserting a plasma extraction filter device in a major vein of a body segment or servicing the body segment containing the edemic tissues, and inserting a return catheter in a major artery of the body segment affected or feeding the body segment from which plasma is extracted. Blood plasma and plasma proteins extracted from the edemic body segment through the plasma extraction filter are directed to an ultrafiltration apparatus where plasma water is separated from the plasma proteins. Plasma proteins are returned to the body segment from which the plasma was extracted via the return catheter in the major artery of the subject body segment. Additional steps and techniques as well as the apparatus used for carrying out the method of the invention will be disclosed in further detail hereinafter.

DETAILED DESCRIPTION OF THE PREFERRED EMBODIMENT

Figure 1:
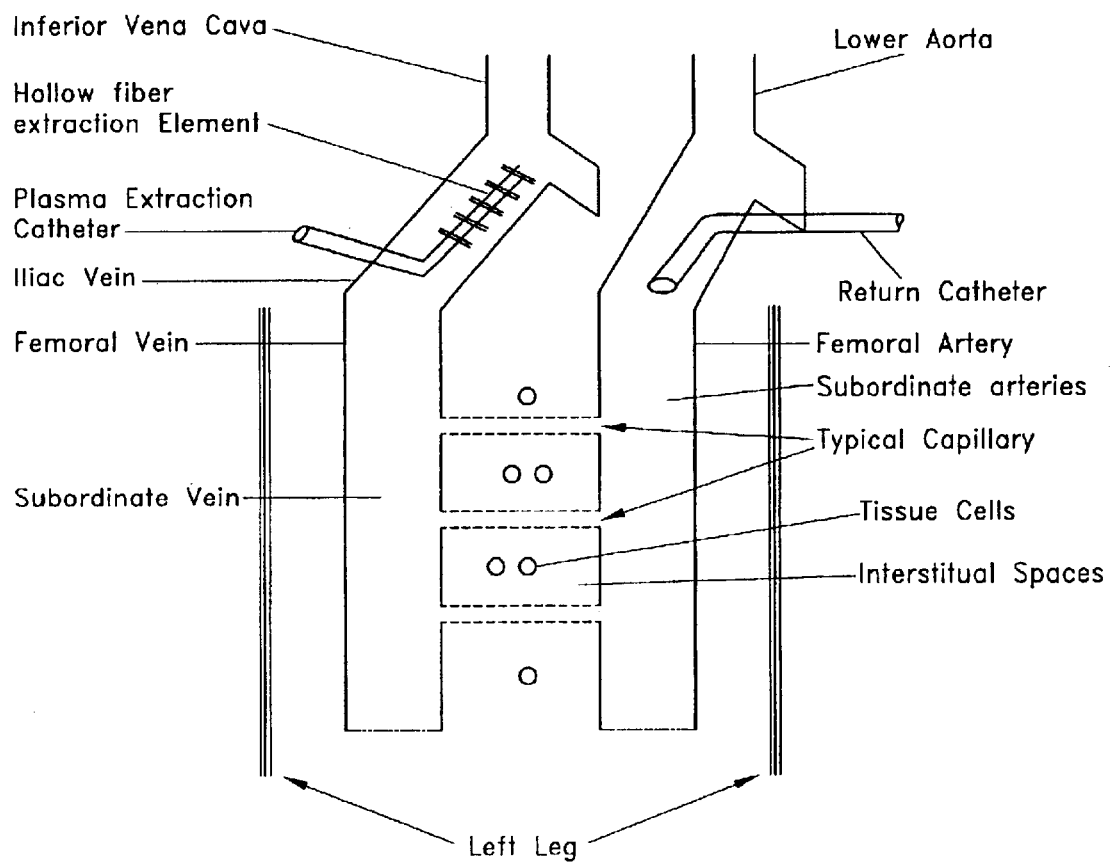
FIG. 1 is a schematic drawing illustrating a typical body segment (left leg) including anatomical structure and placement of a plasma extraction catheter in an appropriate vein and a return catheter in an artery serving the affected body segment.

Referring to FIG. 1, a left leg is schematically illustrated with the iliac and femoral veins extending into a patient's leg from the inferior vena cava, which leg is also fed by the femoral artery extending from the lower aorta. The illustration of the leg also shows subordinate arteries, typical capillaries, tissue cells and interstitial spaces which are affected by the segmented body portion or body segment treatment according to the invention. Localized fluid transfer between the capillaries and interstitial spaces is affected by the differential fluid pressure of the local capillary and interstitial spaces as well as the local plasma colloid osmotic pressure and interstitial colloid osmotic pressure differential. The colloid osmotic pressure in extracellular fluids is a function of the localized concentration of plasma protein, principally albumen. Increasing the localized plasma protein concentration in the capillaries of the affected body segment results in an increase of the colloid osmotic pressure at those sites. By increasing the colloid osmotic pressure, plasma water extraction from the affected edemic interstitial spaces into the capillaries is also increased as is that in the peripheral veins. By removing plasma water from localized capillary circulation, over time, excess cellular water to the interstitial spaces is also removed and lymphatic drainage burden on the compromised lymphatic circulation is also relieved. By removing excess plasma water from the venous circulation immediately proximal to the affected edemic body segment, the systemic circulation and systemic body parts are not affected while edema in the body segment from which the plasma is removed is reduced.

Figure 2:
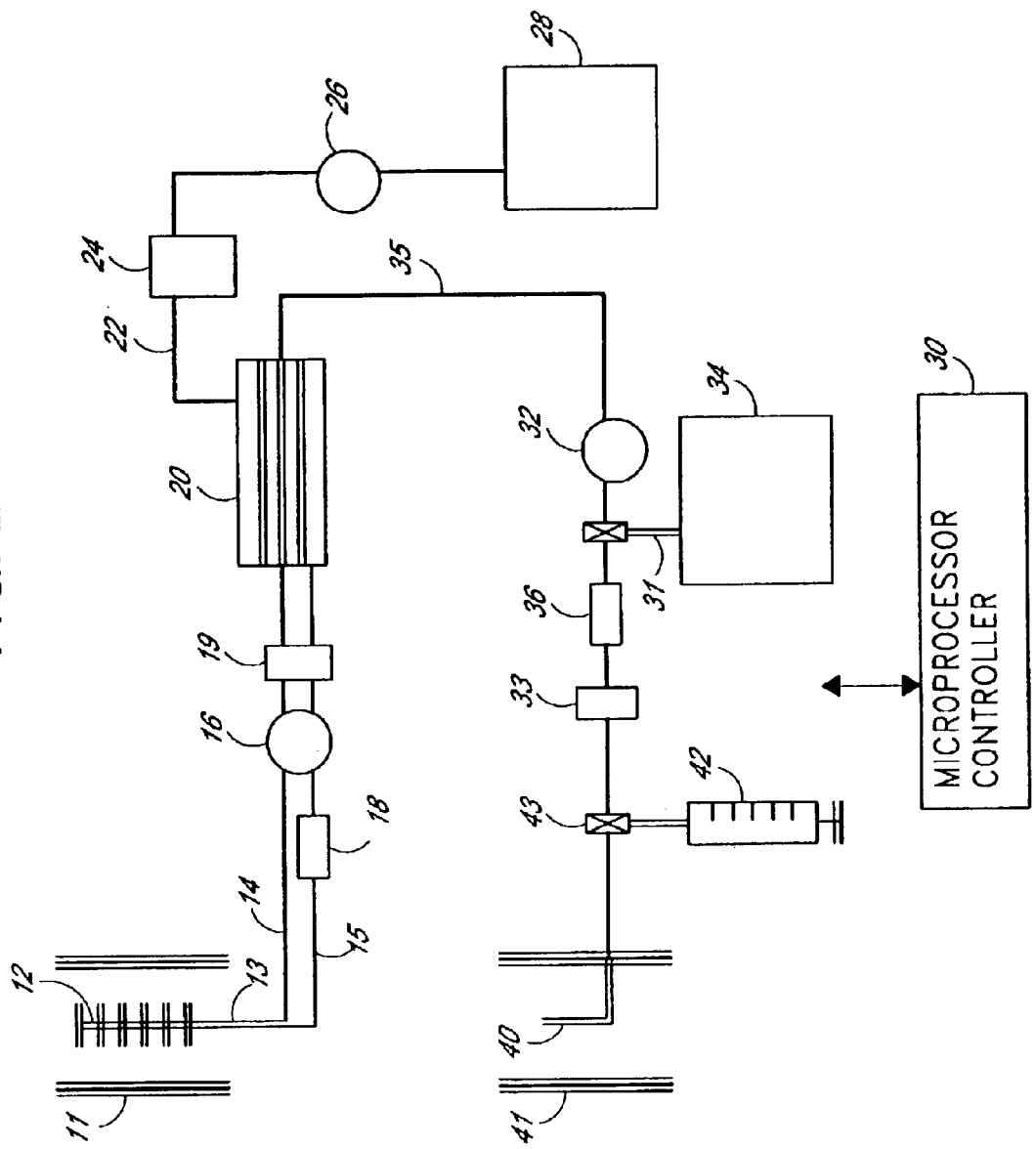
FIG. 2 is a schematic illustration of the plasma extraction and treatment apparatus of the invention.

In FIGS. 1 and 2 there is illustrated schematically the apparatus and treatment of the invention for reducing edema in a typical segmental body part, the left leg specifically referred to in FIG. 1. However, it is to be understood that the principles of treating any other body segment, including either of a patient's legs, arms, peritoneal cavity, neck, etc. will apply, and that shown in FIG. 1 is for the purpose of illustration only. Accordingly, the iliac vein and femoral vein shown for inserting a plasma extraction device and a femoral artery for inserting a plasma protein return catheter are illustrative for treating edema in a person's leg. Although a femoral artery is illustrated in FIG. 1, other arteries such as an iliac artery may be used instead for the return catheter. For example, when treating a patient's arms for edema, major veins useful for inserting the plasma extraction catheter may be the cephalic, auxiliary or basilic veins; major arteries for returning plasma protein which has been extracted include subclaviun, axillary and bronchial arteries. Again, it is to be understood that any major veins and arteries serving the edemic body segment to be treated according to the invention may be used.

Referring to FIGS. 1 and 2, a hollow fiber plasma extraction element or device 12 affixed to the end of a plasma extraction catheter 13 is inserted in the iliac vein 11. The design and structure of the hollow fiber extraction filter device is selected from filter elements and devices disclosed in the aforesaid patents. A preferred plasma filter device incorporates elongated hollow microporous fiber membranes as disclosed therein, and particularly a membrane having the morphology as disclosed in co-pending application Ser. No. 09/549,131, filed Apr. 13, 2000, the description of which is incorporated herein by reference. The specific location for insertion and placement of the hollow fiber extraction device will be in a major vein proximal to the subordinate veins that service the edemic tissues. Specific procedures for inserting the filter are understood by those skilled in the art. Plasma is diffused through the extraction element, and directed from the vein by convection as in the aforesaid patents using one or more positive displacement pumps 16 which operate along the extraction catheter. As illustrated, the extraction catheter 13 is preferably a dual lumen catheter having lumens 14 and 15. A pressure sensor 18 may be located along the catheter, and where two lumens are present, the sensor may be used in one of the lumens, lumen 15, whereby venous pressure may be periodically or selectively sensed by a microprocessor controller 30. The microprocessor controller 30 also monitors other pressure sensors and is operational communication with the pumps as will be discussed further hereinafter. By sensing the pressure in the pressure sensors, the microprocessor controller 30 calibrates trans-membrane pressure and computes trans-membrane flux, thereby measuring the efficacy of the extraction membrane procedure.

The extracted plasma is directed to an ultrafiltration filter assembly 20 where plasma water is separated and removed from the extracted plasma fluid. The separated water is directed along plasma water line catheter 22 via pump 26 to plasma water waste container or bag 28. A pressure sensor 24, also monitored by microprocessor controller 30, is provided in the plasma water line, and in response to the sensed pressure, pump 26 is operated by the microprocessor controller 30. Thus, the rate of plasma water removed and separated is controlled by the monitored pressure sensors 18 and 24, and pumps 16 and 26 are operated in response to the signals sensed by the microprocessor controller 30. Parameters for operating the pumps in response to the sensed pressure are determined by a clinical protocol for treatment of the patient. The clinical protocol may be calculated based upon the degree of edema, in terms of the volume of fluid to be removed, and the acceptable rate of removal based on safe physiological transfer rates of fluids across the capillary bed and the measured osmolality of the arterial blood in the capillaries. The protocol may also take into consideration the practical amount of plasma water that can be removed while also providing adequate liquid remaining in the plasma protein fluid in order to be pumped by pump 32 for returning plasma proteins to the patient or to a protein collection container. As illustrated, after plasma water is separated from the plasma protein fluid in ultrafiltration apparatus 20, the remaining fluid, which contains the desirable plasma proteins to be collected or returned to the patient, is directed via protein fluid line 35 to a protein collection container or bag 34 or to the patient via protein return catheter 40. Pump 32, also a positive displacement pump, is operated by microprocessor controller 30 in response to pressure sensed in pressure sensor 36.

Either or both plasma extraction catheter 13 and protein return line 35 may be dual lumen catheters permitting fluid transfer from and to the blood as well as providing means of sampling both the venous and arterial blood for measurement of appropriate control parameters such as osmolality, hematocrit, and localized pressures. The plasma proteins separated from the plasma water separated in ultrafiltration filter 20 are directed to a protein collection container 34 and/or returned to the patient via protein return catheter 40. The amount of protein returned to the patient may be selected for optimizing the capillary osmolality to a safe clinical protocol. For example a portion of the protein removed from the patient may be collected in a protein collection bag 34 and/or additional protein may be directed to the patient via a medicant syringe 42. Thus, the apparatus and techniques of the invention provide for infusing more or less protein than is removed from the patient to meet the desired patient treatment. A medicant syringe 42 for infusing protein in the return line is illustrated cooperating with a 2-way stopcock 43 for infusing protein in the return line. The syringe may also be used for sampling plasma proteins in return catheter 40. A pressure sensor 36 is also shown in the plasma return line cooperating with microprocessor controller 30 which monitors the pressure and, in response, selectively controls operation of pump 32. Safety sensors 19 and 33 are also illustrated for detecting blood leaks in the extraction membrane assembly and/or a bubble detection sensor for detecting a leak in circuit tubing or components. The protein return catheter 40 is shown inserted in iliac artery 41, by way of example, for treating a patient's leg for edema according to the invention.

Figure 3:
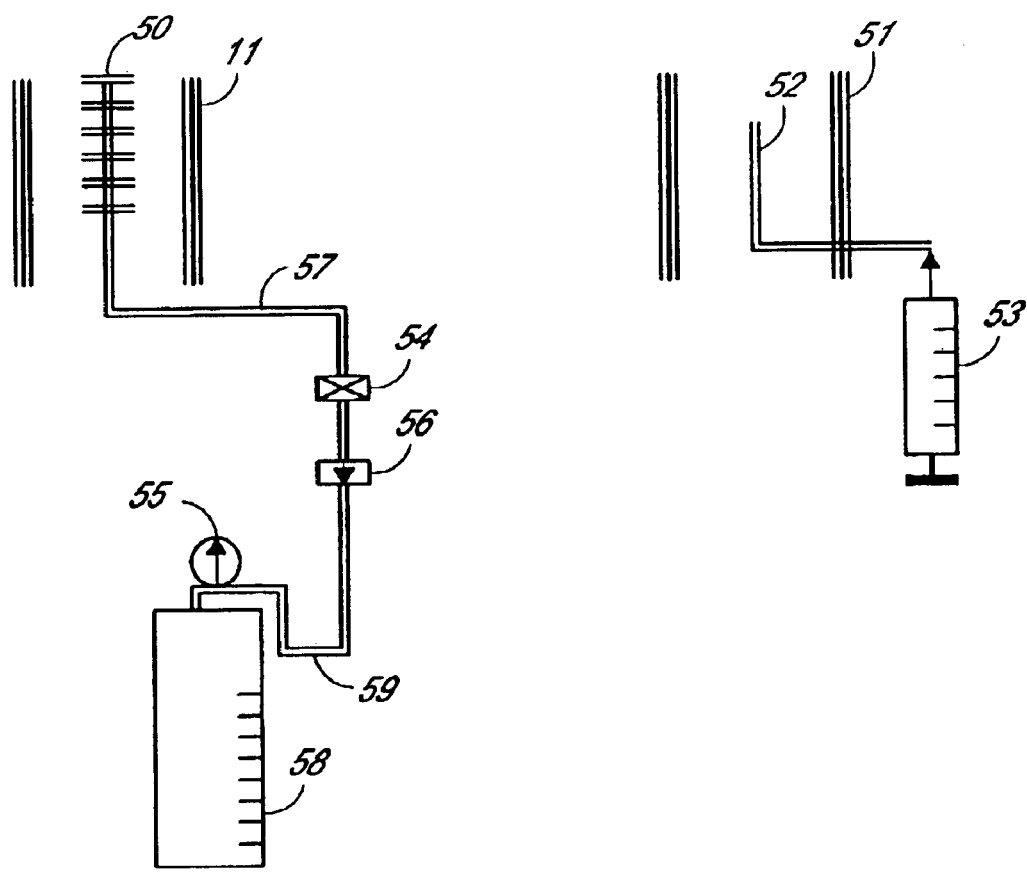
FIG. 3 schematically illustrates another more simplified embodiment of the invention using ultrafiltration membranes.

The aforesaid system configuration is primarily designed for use in more advanced countries and medical facilities where medical and technical support and infrastructure is readily available with efficient and expert use for producing optimal clinical results in a desired period of time. The system illustrated in FIG. 3 is a somewhat simpler and relatively lower cost embodiment which may provide suitable treatment in areas or countries where the aforesaid medical and technical support is not readily available. In the system shown in FIG. 3, a plasma extraction device 50 secured on a single lumen catheter 57 is inserted in a major vein 11 proximal to an affected edemic body segment. The plasma extraction device 50 utilizes ultrafiltration membranes rather than plasma filtration membranes used in the device in FIG. 2 and described above. Such an ultrafiltration membrane has a sieving coefficient and permeability cutoff such that only plasma water is extracted with a cutoff of approximately 2–3,000 daltons instead of plasma filtration membranes which have a cutoff of approximately $_{13}$ 69,000 daltons. Thus, such an ultrafiltration filter device membrane has a pore size allowing only plasma water to be extracted and pass through the filter membrane. In the FIG. 3 apparatus the fluid extraction catheter 57 is connected to an ex-vivo siphon tube 59 for directing plasma water to a collection container 58, for example, a graduated collection bag located approximately 1–2 feet vertically below the extraction element, thus providing a vacuum siphon means for extracting the fluid from the patient's circulation. The collection container 58 also provides means for monitoring the total fluid extracted during a specific therapeutic session. The extraction circuit shown includes a flow orifice 54 and check valve 56. The extraction circuit also contains a mechanical vacuum gauge 55 for permitting the patient to monitor appropriate extraction rates and for adjusting or controlling the rate by raising or lowering the collection container or bag 58 relative to the extraction site, i.e., the location of plasma extraction device 50 in the major vein 11. Another single lumen catheter 52 is inserted in an appropriate artery 51 proximal to the affected edemic body segment and is routed ex-vivo to an injection syringe 53 for providing means of injecting high molecular weight proteins into the capillary system of the edemic body segment, thereby raising osmotic pressure therein. Such increase in osmotic pressure is important in the resulting preferential extraction of plasma water from the edemic space. The injected protein may be blood bank albumen or other nutritious substance such as dextrose. Such features as well as operation of the apparatus illustrated and the advantages thereof for treating segmental edema according to the invention will be evident to those skilled in the art.

What is claimed is:

1. Apparatus for treating segmented edema comprising:
    a plasma extraction device comprising a filter element configured for insertion in a patient's major vein having a plurality of elongated hollow microporous fiber membranes configured to separate plasma including plasma proteins from blood in-vivo within said vein, a plasma extraction catheter communicating with said filter element and in fluid communication with an ultrafiltration apparatus, and a first pump cooperating with said plasma extraction catheter for pumping plasma and plasma proteins to the ultrafiltration apparatus;
    an ultrafiltration apparatus configured to separate plasma water from plasma proteins;
    a plasma water line in fluid communication with the ultrafiltration apparatus configured to direct separated plasma water from the ultrafiltration apparatus; and
    a plasma protein return line in fluid communication with the ultrafiltration apparatus comprising a protein return catheter separate from said plasma extraction catheter and configured to be inserted in a patient's major artery at a location separated from said plasma extraction device wherein said return line is configured to direct plasma proteins to a major artery in the body segment from which plasma is extracted.

2. Apparatus of claim 1 including a second pump cooperating with said plasma water line.

3. Apparatus of claim 2 including a third pump cooperating with said return line for pumping plasma proteins therein.

4. Apparatus of claim 1, 2 or 3 including a first pressure sensor for sensing the pressure in the plasma extraction catheter.

5. Apparatus of claim 2 or 3 including a second pressure sensor for sensing the pressure in the plasma water line.

6. Apparatus of claim 3 including a third pressure sensor for sensing the pressure in the return line.

7. Apparatus of claim 4 including a microprocessor-controller cooperating with said first pressure sensor and said first pump for controlling said pump in response to pressure sensed by said pressure sensor.

8. Apparatus of claim 5 including a microprocessor-controller cooperating with said first and second pressure sensors and said first and second pumps for controlling said pumps in response to pressure sensed by said pressure sensors.

9. Apparatus of claim 6 including a microprocessor-controller cooperating with said first, second and third pressure sensors and said first, second and third pumps for controlling said pumps in response to pressure sensed by said pressure sensor.

10. Apparatus of claim 1 wherein said plasma protein return line is operatively connected to said ultrafiltration apparatus.

11. Apparatus of claim 10 including a protein collection container operatively connected to said plasma protein return line.

12. Apparatus of claim 10 or 11 including a protein sampler device operatively connected to said plasma protein return line.

13. Apparatus of claim 10 or 11 including a fluid injection device operatively connected to said plasma protein return line.

14. Apparatus of claim 10 or 11 including one or more fluid leak detection devices operatively connected to one or more of said plasma extraction catheter, plasma water line or plasma return line.

15. Apparatus of claim 1 including a pump cooperating with said return line for pumping plasma proteins therein.

16. Apparatus for treating edema comprising:
    a plasma extraction filter device configured for insertion in a patient's major vein comprising a filter membrane configured to separate blood plasma including plasma proteins from whole blood in-vivo within said vein, a plasma extraction catheter communicating with said filter device configured to direct said separated blood plasma to an ultrafiltration apparatus, an ultrafiltration apparatus communicating with said plasma extraction catheter configured to separate plasma water from plasma proteins directed thereto by said plasma extraction catheter, a plasma water line configured to direct separated plasma water from the ultrafiltration apparatus, and a plasma protein return line communicating with said ultrafiltration apparatus comprising a protein return catheter separate from said plasma extraction catheter and configured to be inserted in a patient's major artery at a location separated from said plasma extraction device and wherein said return line is configured to direct plasma proteins from the ultrafiltration apparatus to a major artery in the body segment from which plasma is extracted.

17. Apparatus of claim 16 wherein said filter device comprises a plurality of elongated hollow microporous fibers.

18. Apparatus of claim 16 including one or more pumps cooperating with said plasma extraction catheter.

19. Apparatus of claim 16 including one or more pumps cooperating with said plasma water line.

20. Apparatus of claim 16 including one or more pumps cooperating with said return line for pumping plasma proteins therein.

21. Apparatus of claim 16, 19 or 20 including one or more pressure sensors for sensing the pressure in the plasma extraction catheter, and/or said plasma water line, and/or said return line.

22. Apparatus of claim 20 including a microprocessor-controller cooperating with said one or more pressure sensors and said one or more pumps for controlling said one or more pumps in response to pressure sensed by said one or more pressure sensors.

23. Apparatus for treating segmental edema comprising:
    a plasma water extraction device configured to be inserted in a major vein proximal to the body segment containing edemic tissue, said plasma water extraction device comprising an ultrafiltration membrane configured to separate plasma water from blood and plasma protein in-vivo within said vein, a plasma water extraction circuit including a plasma water extraction catheter configured to direct the separated plasma water from the plasma water extraction device, a siphon tube connected ex-vivo to said plasma water extraction catheter configured to direct separated plasma water to a container, a collection container in fluid communication with said syphon tube configured to receive separated plasma water therefrom, and means for monitoring the amount of separated water plasma and/or the rate of plasma water extraction including a vacuum gauge cooperating with said plasma water extraction circuit for monitoring extraction rates.

24. Apparatus of claim 23 wherein said collection container includes graduations for observing the amount of separated plasma water.

25. Apparatus of claim 23 wherein said ultrafiltration membrane comprises a plurality of elongated hollow microporous fibers.

26. Apparatus of claim 23 or 25 wherein said membrane has a permeability cutoff of about 2,000–3,000 daltons.

27. Plasma treatment apparatus comprising:
- a plasma extraction device comprising a filter element configured for insertion in a patient's blood vessel at a first body location having a plurality of elongated hollow microporous fiber membranes configured to separate plasma including plasma proteins from blood in-vivo within said blood vessel, a first catheter extending from said filter element and in fluid communication with an ultrafiltration apparatus, and a first pump cooperating with said first catheter for pumping plasma from the filter element to the ultrafiltration apparatus;
- an ultrafiltration apparatus configured to separate plasma water from the plasma directed thereto;
- a plasma water line in fluid communication with the ultrafiltration apparatus configured to direct separated plasma water from the ultrafiltration apparatus; and
- a return line in fluid communication with the ultrafiltration apparatus comprising a second catheter separate from said first catheter and configured to be inserted in a patient's blood vessel at a second body location separated from said first body location for directing plasma proteins therein.

28. Apparatus of claim 27 including one or more pumps cooperating with said first catheter.

29. Apparatus of claim 27 including one or more pumps cooperating with said plasma water line.

30. Apparatus of claim 27 including one or more pumps cooperating with said return line.

31. Apparatus of claim 27, 28, 29 or 30 including one or more pressure sensors for sensing the pressure in the first catheter, and/or said plasma water line, and/or said return line.

32. Apparatus of claim 31 including a microprocessor-controller cooperating with said one or more pressure sensors and said one or more pumps for controlling said one or more pumps in response to pressure sensed by said one or more pressure sensors.

33. Apparatus of claim 27 including a fluid injection device operatively connected to said return line.

34. Apparatus for treating segmented edema comprising:
- a plasma extraction device comprising a filter element configured for insertion in a patient's major vein having a plurality of elongated hollow microporous fiber membranes configured to separate plasma including plasma proteins from blood in vivo within said vein, a plasma extraction catheter extending therefrom in fluid communication with an ultrafiltration apparatus, and a first pump cooperating with said plasma extraction catheter for pumping plasma and plasma proteins to the ultrafiltration apparatus;
- an ultrafiltration apparatus configured to separate plasma water from plasma proteins;
- a plasma water line in fluid communication with the ultrafiltration apparatus configured to direct separated plasma water from the ultrafiltration apparatus; and
- a plasma protein return line in fluid communication with the ultrafiltration apparatus including a protein catheter configured to direct plasma proteins to a major artery in the body segment from which plasma is extracted.

35. Apparatus of claim 34 including a second pump cooperating with said plasma water line.

36. Apparatus of claim 35 including a third pump cooperating with said return line for pumping plasma proteins therein.

* * * * *